United States Patent [19]

Brandfield

[11] Patent Number: 5,047,037
[45] Date of Patent: Sep. 10, 1991

[54] SUTURE REMOVING INSTRUMENT

[76] Inventor: Robert T. Brandfield, 30 Beechwood, Oakland, Calif. 94618

[21] Appl. No.: 464,092

[22] Filed: Jan. 12, 1989

[51] Int. Cl.⁵ .............................................. A61B 17/28
[52] U.S. Cl. .................................. 606/138; 606/211; 30/124
[58] Field of Search .............. 606/138, 120, 167, 170, 606/175, 205–207, 210, 211; 294/99; 30/124, 134

[56] References Cited

U.S. PATENT DOCUMENTS

| | | | |
|---|---|---|---|
| 2,998,649 | 9/1961 | Miller et al. | 606/211 |
| 3,054,182 | 9/1962 | Whitton | 606/211 |
| 3,443,313 | 5/1969 | Profy | 30/134 |
| 3,576,072 | 4/1971 | Foster | 30/124 |
| 3,624,683 | 11/1971 | Matles | 30/124 |
| 3,659,343 | 5/1972 | Straus | 30/124 |
| 3,879,846 | 4/1975 | Allen, Jr. | 606/211 |
| 4,034,473 | 10/1977 | May | 606/138 |
| 4,053,979 | 7/1977 | Tuthill et al. | 606/138 |
| 4,246,698 | 1/1981 | Lasner et al. | 30/134 |
| 4,669,470 | 6/1987 | Brandfield | 606/207 |

*Primary Examiner*—C. Fred Rosenbaum
*Assistant Examiner*—William W. Lewis
*Attorney, Agent, or Firm*—Townsend and Townsend

[57] ABSTRACT

A forceps-like device with scored surfaces on the inside of the tips of two arms for grasping a suture. A blade is provided on the inside of one arm just behind the tip. The blade does not contact the other arm when a light amount of compression force is applied to grasp a suture. By applying a greater amount of compression force, the arms are further compressed behind the tips, pushing the blade into contact with an anvil surface on the opposite arm, allowing it to cut a suture positioned in-between.

3 Claims, 1 Drawing Sheet

SUTURE REMOVING INSTRUMENT

BACKGROUND

The present invention relates to forceps or scissors used for removing sutures. Several instruments have been devised to allow one instrument to be used for grasping a suture and for cutting the suture. One such forceps-scissors combination is shown in U.S. Pat. No. 4,669,470. Other relevant apparatus are shown in U.S. Pat. Nos. 3,443,313, No. 4,034,473, No. 4,053,979 and French applications No. 1183358 and No. 2371912.

Unfortunately, in the '470 patent, one arm of the scissors portion of the forceps must be forced beneath the suture to cut it. This can be awkward for the surgeon and uncomfortable for the patient. In addition, scissors are often difficult to use by surgeons in other than their favored hand.

SUMMARY OF THE INVENTION

The present invention provides a forceps-like device with scored surfaces on the inside of the tips of two arms for grasping a suture. A blade is provided on the inside of one arm just behind the tip. The blade does not contact the other arm when a light amount of compression force is applied to grasp a suture. By applying a greater amount of compression force, the arms are further compressed behind the tips, pushing the blade into contact with an anvil surface on the opposite arm, allowing it to cut a suture positioned in-between.

The anvil surface and the blade are attached so that when the proper amount of compression is applied, the blade is flush with the anvil to provide an even cutting surface. This is accomplished by providing the appropriate amount of bend near the tip of the forceps. With the tips in contact, the portion of the forceps closest to the tip will bend the least under further compression, while the portion furthest from the tips will bend more, thus adjusting the position of the arms so that when the anvil surface does come in contact with the blade, it will be flush with it.

By positioning the blade immediately behind the tips, a surgeon can grasp the suture first, and then with a slight forward movement, cut the suture. Alternately, the surgeon can grasp the suture, and by tilting the forceps to position a rearward portion of the suture between the blade and anvil, can then cut the suture by simply compressing the forceps slightly more. All this time, the surgeon has his other hand free for use in holding the patient.

Preferably, a guide pin is provided in one forceps arm to extend into a matching hole on the other forceps arm to maintain alignment of the forceps arms during compressing. Preferably, when the forceps is compressed sufficiently to grasp the suture, the blade will be approximately one-half the diameter of the suture from the anvil surface. The anvil surface itself is a hardened portion of the tip which may be integral with the arm of the forceps or separately attached.

For a further understanding of the nature and advantages of the invention, reference should be made to the ensuing detailed description taken in conjunction with the accompanying drawings.

DETAILED DESCRIPTION OF THE PREFERRED EMBODIMENT

Figure 1:
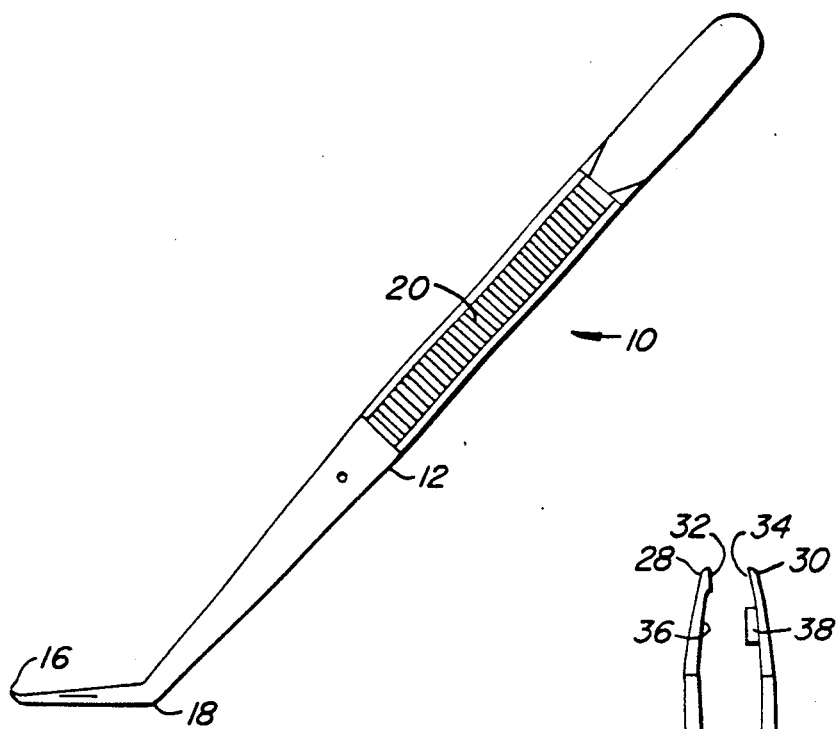
FIG. 1 is a side view of the suture remover instrument according to the present invention in working position.

FIG. 1 shows a suture remover instrument 10 according to the present invention. An arm 12 is visible in FIG. 1, with an opposing arm 14 being visible in FIGS. 2A and 2B. Arm 12 has an inwardly bent portion near its tip 16, with the arm being bent as shown at a junction 18. This allows the upper portion of the arm to be easily grasped while sliding the lower portion between tip 16 and bend 18 across the patient's skin up to a suture. A scored area 20 is provided for easy grasping with the surgeon's fingers.

Figures 2A, 2B:
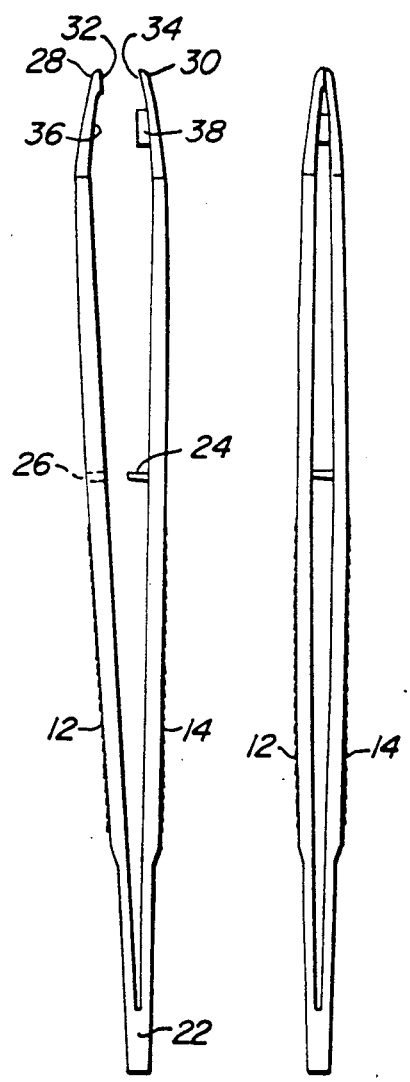
FIGS. 2A and 2B are top views of the instrument of FIG. 1 showing the arms in open and fully compressed positions, respectively.

FIG. 2A shows that arms 12 and 14 are joined at an end 22. Near the middle of the arms is an inwardly protruding pin 24 on arm 14 which is matched with an opposite hole 26 in arm 12. Pin 24 will be guided into hole 26 to maintain arms 12 and 14 in alignment. Tips 28 and 30 of arms 12 and 14, respectively, have inside surfaces 32 and 34, respectively, which are scored. These surfaces are used to grasp a suture during compression.

Arm 12 has an inner anvil surface 36 behind tip 28. This is opposed by a protruding blade 38 on arm 14. As can be seen in FIG. 2B, when the arms 12 and 14 are compressed, blade 38 will come in contact with anvil surface 36, providing a cutting action for a suture positioned in-between.

Figures 3A, 3B:
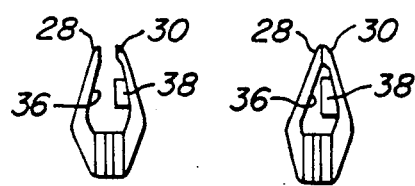
FIGS. 3A and 3B are end views of the instrument of FIGS. 1 and 2, showing the tips in open and partially compressed positions, respectively.

As shown in FIG. 3B, viewed from the far end 22 of the forceps, during slight compression tips 28 and 34 are in contact while blade 38 is separated from anvil surface 36. The distance between blade 38 and anvil surface 36 is preferably approximately one-half the diameter of the suture being cut. Anvil surface 36 is a hard surface that will stand up to the compression of the blade against it. As can be seen, in the view of FIG. 3B, the gap between blade 38 and surface 36 is narrower towards the tip of the arms than further away from the tips. However, as the arm is further compressed, the portion near the tips will move less than the portion further from the tips due to the fact that the tips are already in contact, and thus provide a resisting force. The result will be that by the time the portion near the tips contacts blade 38, all of blade 38 will be in contact with surface 36.

As can be seen from FIGS. 2A and 2B, the arms 12 and 14 diverge from each other near end portion 22, and then gently curve inward to converge near their tips 28 and 34. The suture is cut by holding the suture material taut with scored surfaces 32 and 34 and then providing a sharp knife contact with blade 38 at the proper angle to the suture, with blade 38 being compressed against surface 36.

The present invention provides a very slender, flat, non-cutting arm 12 on one side which can be comfortably passed beneath the suture, thus serving as a holder or anvil for the opposite blade 38. The arms can be moved independently towards the opposite arms only far enough to produce the desired tension. By inwardly curving the tips at the appropriate angle, they can be used for grasping, setting and removing a suture while avoiding contacting and thus dulling the blade when no cutting is desired.

The present invention provides the function of two instruments in one, a forceps which would normally be used in one hand and a scissors which would normally be used in the other hand. Both can now be used in a single hand, freeing the other hand of the surgeon. This allows non-ambidextrous people to remove sutures. Many people who would remove sutures, such as nurses and paramedics, may not be as skilled with their hands as a surgeon. The present invention also allows one hand to be free to steady the suture body part, which is very important for removing sutures in children and anxious patients, and would otherwise require another person to assist. Also, the present invention allows economy in manufacturing, re-sterilizing and storing by using one simple instrument where two have been required in the past.

As will be understood by those of skill in the art, the present invention could be embodied in many specific forms without departing from the spirit or essential characteristics thereof. For example, blade 38 could be oriented at a slightly different angle than in line with the arm. Accordingly, the disclosure of the preferred embodiment of the invention is intended to be illustrative, but not limiting of the scope of the invention which is set forth in the following claims.

What is claimed is:

1. A forceps comprising:
   a pair of elongate, planar arms coupled together at a first end and tapering towards a second end of each arm;
   a pair of scored surfaces on the inside of said arms at said second ends;
   a blade having a limited length compared to said forceps and extending from the inside of a first one of said arms, near said second end, toward a second one of said arms;
   an anvil surface on the inside of said second arm opposite said blade, said anvil surface being shaped to provide even contact with said blade when said arms are fully compressed;
   said arms being formed to provide a compressible spring action so that said second ends of said arms are separated with no compression force being applied, said scored surfaces contact each other without said blade contacting said anvil surface with a first amount of compression force applied to the outside of said arms, and said blade contacting said anvil surface with a second amount of compression force applied to the outside of said arms, said second compression force being greater than said first compression force; and
   an inwardly extending peg coupled to the inside surface of one of said arms, and a hole matching the diameter of said peg positioned in the other of said arms opposite said peg, so that said peg will extend into said hole during compression of said arms together to provide a guiding action for said arms on compression.

2. A forceps comprising:
   a pair of elongate, planar arms coupled together at a first end and tapering towards a second end of each arm;
   a pair of scored surfaces on the inside of said arms at said second ends;
   a blade extending from the inside of a first one of said arms toward a second one of said arms, a portion of said blade being within one-quarter inch of the endmost portion of the second end of said first arm;
   an anvil surface on the inside of said second arm opposite said blade, said anvil surface being shaped to provide even contact with said blade when said arms are fully compressed;
   said arms being formed to provide a compressible spring action so that said second ends of said arms are separated with no compression force being applied, said scored surfaces contact each other without said blade contacting said anvil surface with a first amount of compression force applied to the outside of said arms, and said blade contacting said anvil surface with a second amount of compression force applied to the outside of said arms, said second compression force being greater than said first compression force, said blade being separated from said anvil surface by approximately one-half the diameter of said suture with said first amount of compression force being applied; and
   an inwardly extending peg coupled to the inside surface of one of said arms, and a hole matching the diameter of said peg positioned in the other of said arms opposite said peg, so that said peg will extend into said hole during compression of said arms together to provide a guiding action for said arms on compression.

3. A forceps comprising:
   a pair of elongate, planar arms coupled together at a first end and tapering towards a second end of each arm, a tapered portion of said arms at said second end being at an angle to a first portion of said arms extending to said first end;
   a pair of scored surfaces on the inside of said arms at said tapered portions;
   a blade extending from the inside of a first one of said arms toward a second one of said arms at said tapered portion;
   an anvil surface on the inside of said second arm opposite said blade at said tapered portion, said anvil surface being shaped to provide even contact with said blade when said arms are fully compressed;
   said arms being formed to provide a compressible spring action so that said second ends of said arms are separated with no compression force being applied, said scored surfaces contact each other without said blade contacting said anvil surface with a first amount of compression force applied to the outside of said arms, and said blade contacting said anvil surface with a second amount of compression force applied to the outside of said arms, said second compression force being greater than said first compression force.

* * * * *